United States Patent
Liu

(10) Patent No.: US 10,401,362 B2
(45) Date of Patent: Sep. 3, 2019

(54) MICROFLUIDIC DEVICE FOR CELL CAPTURE AND ISOLATION

(71) Applicant: Lehigh University, Bethlehem, PA (US)

(72) Inventor: Yaling Liu, Ambler, PA (US)

(73) Assignee: Lehigh University

( * ) Notice: Subject to any disclaimer, the term of this patent is extended or adjusted under 35 U.S.C. 154(b) by 396 days.

(21) Appl. No.: 14/618,246

(22) Filed: Feb. 10, 2015

(65) Prior Publication Data

US 2015/0226741 A1    Aug. 13, 2015

Related U.S. Application Data

(60) Provisional application No. 61/937,709, filed on Feb. 10, 2014.

(51) Int. Cl.
  *G01N 33/574*    (2006.01)
  *G01N 33/543*    (2006.01)
  *B01L 3/00*    (2006.01)

(52) U.S. Cl.
  CPC ...... *G01N 33/574* (2013.01); *B01L 3/502753* (2013.01); *G01N 33/54373* (2013.01); *B01L 2300/0816* (2013.01); *B01L 2300/0896* (2013.01); *B01L 2400/086* (2013.01)

(58) Field of Classification Search
  CPC ..... B01L 2300/0816; B01L 2300/0896; B01L 2400/086; B01L 3/502753; G01N 33/54373; G01N 33/574
  See application file for complete search history.

(56) References Cited

PUBLICATIONS

Wang et al., "Highly Efficient Capture of Circulating Tumor Cells by Using Nanostructured Silicon Substrates with Integrated Chaotic Micromixers," Angew. Chem. Int. Ed., 2011, vol. 50, issue 13, pp. 3084-3088.*
Stroock et al., "Chaotic Mixer for Microchannels," Science, 2002, vol. 295, issue 5555, pp. 647-651.*
Thomas et al., "Micro-patterned Surface for Efficient Capturing of Circulating Tumor Cells," Bioengineering Conference (NEBEC), 2012 38th Annual Northeast, pp. 416-417; publisher IEEE.*
Wang et al., "Three-Dimensional Nanostructured Substrates toward Efficient Capture of Circulating Tumor Cells," Angew. Chem. Int. Ed., 2009, vol. 48, issue 47, pp. 8970-8973.*
Hsu et al., "Wafer-scale silicon nanopillars and nanocones by Langmuir-Blodgett assembly and etching," 2008, Appl. Phys. Lett., vol. 93, p. 133109.*
Wang et al., "Effects of nanopillar array diameter and spacing on cancer cell capture and cell behaviors," Nanoscale, Nov. 7, 2014, vol. 6, No. 21, pp. 12482-12489.*

* cited by examiner

*Primary Examiner* — Galina M. Yakovleva
(74) *Attorney, Agent, or Firm* — The Belles Group, Inc.

(57) ABSTRACT

Described herein are devices for capturing or isolating a biological cell from a sample, the device comprising a capture bed comprising a wave-herringbone surface pattern; and a plurality of nanostructures. Methods of making and using the same are also described.

12 Claims, 6 Drawing Sheets

MICROFLUIDIC DEVICE FOR CELL CAPTURE AND ISOLATION

CROSS-REFERENCE TO RELATED PATENT APPLICATION

This application claims the benefit of U.S. Provisional Application Ser. No. 61/937,709, filed Feb. 10, 2014, entitled "Microfluidic Devices and Methods of Using Same", the contents of which are hereby incorporated herein in their entirety.

BACKGROUND

Non-invasive in nature, blood tests are the most commonly performed screening and diagnostic tests to reveal a rich amount of information of one's health state, ranging from chemistry and serology to hematology and immunohematology. Recently, disease specific cells existing in extremely low concentration in blood have been identified as new diagnostic and prognostic markers. For example, circulating tumor cells (CTCs) in peripheral blood are recognized as a critical cellular link between the primary malignant tumor and the peripheral metastases of patients with lung, prostate, colon, breast, liver, and ovarian cancers. However, current technology platforms lack the ability to reliably separate and detect rare cells in an extremely low quantity, down to 1-10 cells per billion red blood cells. As a result, there is no "gold standard" rare-event analysis method for measuring rare cells such as CTCs.

Conventional cell separation techniques including density gradient centrifugation, preferential lysis of red blood cells, ficoll-hypaque density centrifugation, porous filters and immunoaffinity chromatography, rely on size, density, rigidity and specific surface antigens to isolate desired cell subpopulations. These methods usually require laborious manual and bulk sample preparation steps, resulting in highly variable results and low sensitivity. The more recent molecular methods such as PCR-based detection, suffer from loss of live cells for other analysis.

Several rare-event imaging systems, including the rare event imaging system (REIS), fiber optic array scanning technology (FAST), and automated digital microscopy, have been developed to store images for re-examination without actual cell recovery. However, the number of cells to be evaluated to find rare cells is prohibitively large and the imaging modalities are rather cumbersome and complicated.

In comparison, lab-on-a-chip microfluidic devices have become increasingly attractive for blood analysis as they allow for gentle manipulation and precise control of microenvironment of individual cells in blood. However, none of the existing lab-on-a-chip approaches based on cell physical properties have offered reliable and rapid isolation of CTCs from the whole blood with minimal sample preparation.

Immunoaffinity cell isolation uses antibodies recognizing CTC specific surface antigens to achieve high specificity. However, the sensitivity of CTC detection is low and highly variable for clinical applications.

Although progress in the technology space has been made, in order to explore the benefits of CTCs in metastatic cancer, there is a need to develop cell sorting technologies that specifically target rare CTCs while meeting the sensitivity, purity, high throughput, live cell and automation requirements. Embodiments of the present invention are directed to meeting these needs.

SUMMARY

Some embodiments of the present invention provide a microfluidic device comprising a 3D hierarchically structured substrate—specifically, a microscale rippled surface decorated with nanopillar array or nanoparticles to accommodate the multi-scale characteristic dimensions of cancer cells and optimize cell capture in a microfluidic platform.

In some embodiments, embodiments of the present invention comprise a substrate comprising hierarchical surfaces that mimic natural surfaces; and therefore, maximize efficiency. For example, the small-intestine has a folded/rippled surface (plicae circularizes), villi, and microvilli, which increase the absorptive surface area by several folds. Many cells, including cancer cells, are also found to contain membrane extrusions on the order of 100 nm for effective interactions with the environment.

In some embodiments, embodiments of the present invention comprise multi-scale structures to match both the cell dimension and membrane extrusions, respectively.

In some embodiments, the microscale surface in the form of ripples or herringbones aims to create hydrodynamic force to improve cell-surface collision frequency. When blood flows in a microchannel under a laminar flow, the large number of red blood cells easily shields the rare CTCs from the antibody coated substrate. In addition, the low shear region near any surface in the flow stream creates a thin lubrication layer to limit the number of contacts between the cells and the antibody-coated surfaces. A microstructured substrate is expected to improve the collision between the cell and antibody-coated walls through microvortex or centrifugal flow patterns.

It is believed that micro-/nanostructured surfaces, including nanoposts, nanowires and nanoparticles, not only increase surface area, but also enhance local topographic interactions with cell membrane structures such as microvilli and filopodia, which in turn benefits both capture efficiency and specificity.

Some embodiments of the present invention provide herringbone structures with smoothly curved undulations through created through surface buckling, which will eliminate the low shear sharp corners prone to non-specific binding. The smoothly curved undulation is also expected to reduce high shear regions in the sharp-corner devices, causing less damage to the cells. Alternatively, parallel microripples may be fabricated to induce centrifugal forces to encourage cell/substrate collision.

In some embodiments, the engineered nano-structures will match the size and density of microvilli on a tumor cell membrane, which have an average radius of 50 nm, length of 2 µm, and density of 13 per 100 µm$^2$. Since the microvilli on leukocytes are thicker in diameter compared to cancer cells by a couple of hundred nanometers, embodiments of the present invention are designed to have improved size complementarity between the capture bed and cancer microvilli, which is expected to enhance cell-surface adhesion strength and encourage specific tumor cell capture. In some embodiments, the flexibility of the nanostructures is modified by creating them in different soft materials with Young's moduli ranging from MPa to KPa to reduce potential cell damage. In some embodiments, the combination of nanostructure and soft materials will allow for enhanced local topographic interactions with the nanoscale components of the cellular surface (e.g., microvilli and filopodia), leading to vastly improved cell-capture affinity compared to unstructured surfaces or surfaces with a single scale feature.

Some embodiments provide multiscale topographies: e.g., microscale for hydrodynamic effect and nanoscale for nanostructure interactions to promote isolation of rare cells in an immunoaffinity microfluidic chip.

In some embodiments, the surface has three distinct features. In some embodiments, these features enhance both rare cell capture efficiency (number of captured cells/total number of target cells) and selectivity (captured target cells/total number of captured cells). Some embodiments provide:

1) a microscopic wavy surface (1D ripples or 2D herringbones) will be fabricated to enhance cell margination and binding. The pattern, wavelength, and amplitude may be fine-tuned to enable larger surface contact area for cell and optimal hydrodynamic efficiency. In some embodiments, due to the non-uniform shear stress distribution, the majority of captured cells will be located in the troughs of the periodic waves, allowing for accurate cell counting;

2) nanopillar arrays or nanoparticles that match the nanostructures on the cell surface (e.g. microvilli or filopodia) designed and integrated with the above fabricated microscopic wavy patterns to enhance cell-wall interaction and adhesion strength;

3) controlled flow shear rate in a microfluidic channel to allow specific cell capture; and 4) minimized non-specific binding as a result of the smoothly curved microstructures.

DETAILED DESCRIPTION

The present inventors have developed a computational model for studying transport and adhesion dynamics of particles and cells, e.g., arbitrarily-shaped objects under fluid flow. As the present inventors have discovered, cell capture rates are largely influenced by surface morphology.

In some embodiments, the present invention provides methods of capturing a cell or a particle from a biological sample. In some embodiments, the method comprises the step of flushing the capture bed after it is contacted with a sample, to measure the adhesion strength of a captured cell. In some embodiments, the method demonstrates the higher adhesion strength provided by a larger curved contact area.

In some embodiments, shear rate is used to control the selectivity of the capture process. In some embodiments, the methods of the present invention take advantage of the fact that tumor cells have over expressed biomarkers on their membranes. Some embodiments of the present invention provide methods that separate tumor cells from white blood cells (WBCs). For example, the expression levels of the epidermal growth factor receptor (EGFR) or epithelial cell adhesion molecule (EpCAM) in cancer cells can be ~100 times higher than those in normal cells. With higher adhesion receptor density on the membrane, CTC cells require a larger shear force to detach from surfaces coated with corresponding antibodies. By controlling the shear rate within a certain range, CTC might be able to adhere to the surface while WBC will be washed away. The computational results agree well with the experimentally data with primary human glioblastoma (hGBM) cells (a surrogate for CTCs).

In some embodiments, the shear rate required to separate CTCs from WBCs is from about 20 $s^{-1}$ to about 200 $s^{-1}$. In some embodiments, the shear rate required to separate CTCs from WBCs is from about 20 $s^{-1}$ to about 175 $s^{-1}$. In some embodiments, the shear rate required to separate CTCs from WBCs is from about 20 $s^{-1}$ to about 150 $s^{-1}$. In some embodiments, the shear rate required to separate CTCs from WBCs is from about 20 $s^{-1}$ to about 125 $s^{-1}$. In some embodiments, the shear rate required to separate CTCs from WBCs is from about 20 $s^{-1}$ to about 100 $s^{-1}$. In some embodiments, the shear rate required to separate CTCs from WBCs is from about 20 $s^{-1}$ to about 80 $s^{-1}$. In some embodiments, the shear rate required to separate CTCs from WBCs is from about 20 $s^{-1}$ to about 60 $s^{-1}$. In some embodiments, the shear rate required to separate CTCs from WBCs is from about 20 $s^{-1}$ to about 40 $s^{-1}$.

Figure 4:
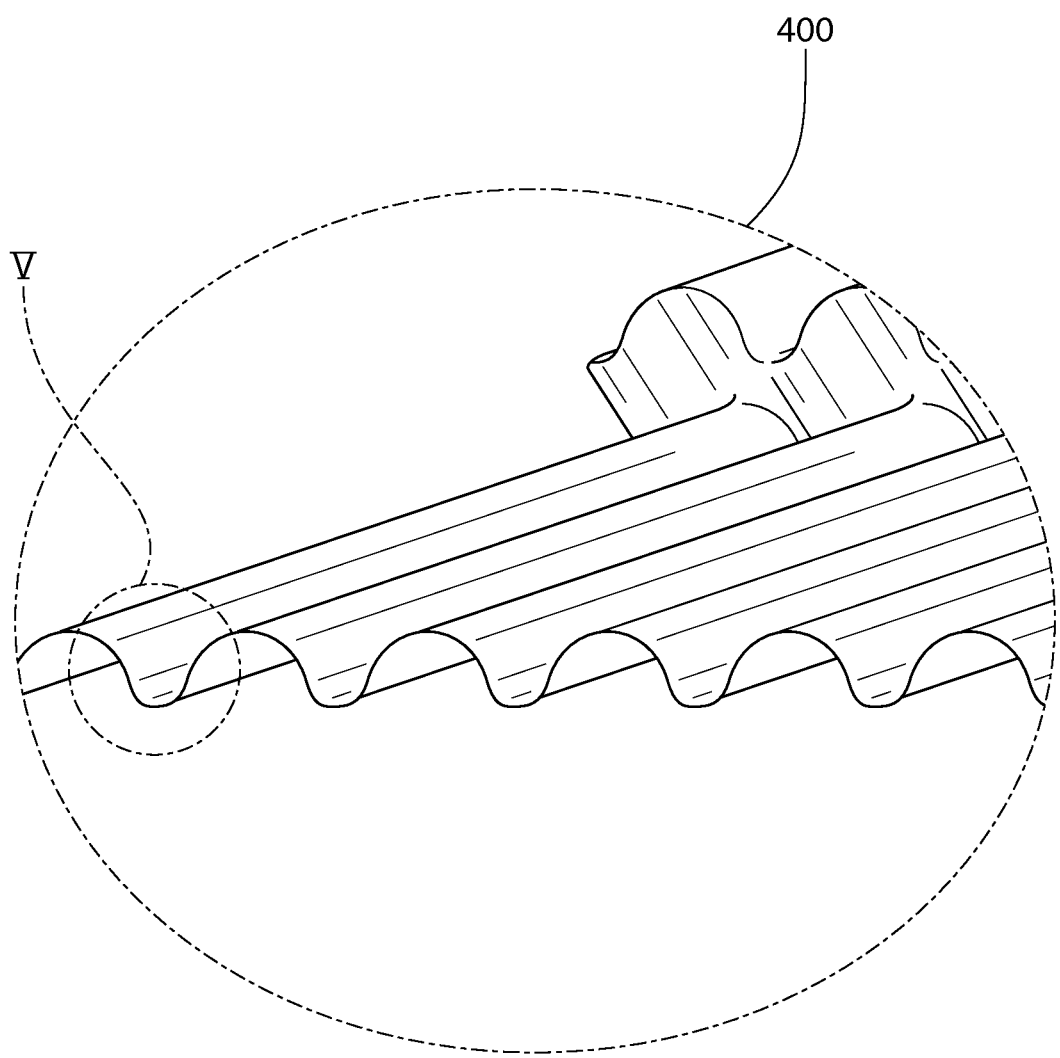
FIG. 4 depicts a side view zoom of an exemplary hierarchical surface pattern of the present invention.
Figure 6:
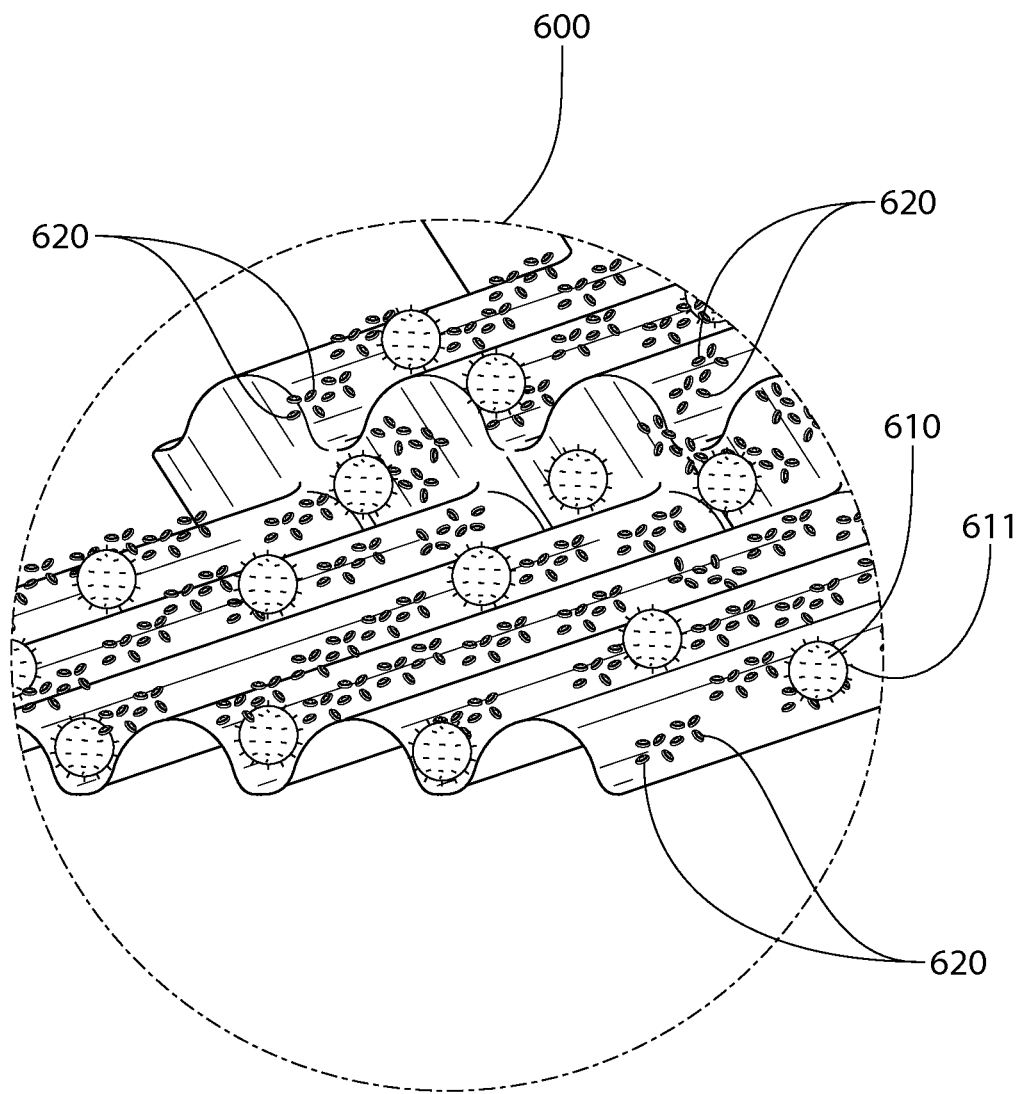
FIG. 6 depicts a side view zoom of cell trapping in an exemplary surface pattern of the present invention.

In some embodiments, the device is configured to generate microvortices inside the capture bed to increase cell-wall collision frequency and avoid a flow recirculation vortex near the capture wall surface, which could potentially lead to non-specific trapping of cells. For example, the cross-sectional view depicted in FIG. 6, shows chaotic microvortices that help cells mix and collide with the wall. FIG. 4 provides a side view having a smooth shear flow near the rippled surface, which will not trap cells like traditional rectangular microgrooves. In some embodiments, a Dean Number of 35.9 is the threshold value for the onset of flow instability. Dean number is calculated using the following equation:

$$De=(pvD/\mu)(D/2R)^{1/2}$$

wherein R is the radius of curvature; and

D is the hydraulic diameter of the channel.

Another advantage of the inventive design is the minimization of areas with high shear forces that may damage the cells. The actual flow patterns for complex geometries such as the inventive wave-herringbone surface pattern may be created and optimized using computational fluid dynamics simulation. In some embodiments, wavelength and channel height are optimized to maximize cell-wall collision and increase capture efficiency.

In some embodiments, the micro-structured surface pattern comprises a PDMS/oxide bilayer. In some embodiments, the micro-structured surface is prepared by buckling of the PDMS/oxide bilayer, wherein the pattern and wavelength of the wavy surface is determined through computational modeling. In some embodiments, a wave-herringbone surface pattern is then replicated on stress-free films, e.g. PDMS. PDMS is selected here due to its biocompatibility, low modulus, and wide knowledge of its applications in microfluidics.

In buckling, the wavelength (λ) and amplitude (A) of the wrinkles can be tuned by varying the elastic modulus of the PDMS substrate and the thickness of the top silicate layer, which are controlled by the mixing ratio of the PDMS resin/crosslinker, UVO/O2 exposure time, the modulus and thickness of the hard layer, and the applied strain.

In general, the aspect ratio of the surface patterns of the present invention are ≤0.3(A/λ). In some embodiments, wrinkles can evolve from 1D ripples into various 2D patterns, including bifurcated wrinkles, labyrinths, and herringbones, depending on the anisotropy of the applied forces and stress release sequence, which will guide the energy release path. In some embodiments, the wrinkle size and shape are fine-tuned to produce wave-herringbone patterns that generate efficient microvortices for cell-wall collision while reducing non-specific cell trapping.

In some embodiments, the fabricated PDMS pattern is directly used in the capture bed of the microfluidic devices of the present invention. In some embodiments, the PDMS surface is functionalized with specific capturing agents, e.g. antibodies. In other embodiments, the PDMS patterns can be used as molds to replicate on different substrates with very different Young's moduli, including epoxy, hydrogels (e.g. poly(2-hydroxyl ethyl methacrylate, PHEMA, and polyacrylamide), PMMA, and poly(styrene) (PS) using established soft lithography techniques, such as replica molding, nanoimprint and capillary force lithography.

In some embodiments, the antibody will be coated on these materials through standard chemistry to functionalize a hydroxyl group, carboxyl group (directly or from hydrolyzed ester group), amine group, or simply though physisorption.

In some embodiments, to create pillar arrays on a microripple surface, a PDMS pillar array is fabricated, which will then be stretched, followed by $O_2$ plasma or UVO treatment. In some embodiments, after release of strain, microripples are formed with built-in pillars. The wavelength and amplitude of the microripples may be determined by stretching strain level, plasma or UVO treatment time and power, as well as the Young's modulus of the PDMS film—similar to wrinkle formation on bulk PDMS film.

In some embodiments, the tilt angle of the pillars is determined by the stretching angle between stretching direction, x, and pillar lattice axis, k. In some embodiments, the degree of pillar tilting on wrinkles is highly dependent on PDMS film thickness.

In some embodiments, after stretching and oxygen plasma treatment, the PDMS bilayer film is dip-coated with silica nanoparticles to introduce nano-scale roughness, which can be subsequently functionalized with silane and a specific antibody. After releasing the initial strain, the dual-structured surface is obtained. Alternatively, a microcontact printing technique to pick up the nanoparticles using a stretched PDMS wrinkled surface can be used.

In both hierarchical structures, the wavelength/amplitude of the microripples, the wave-herringbone surface pattern, the size of nanoparticles, pillar diameter, spacing, and aspect ratio are designed to match microvilli structure. The density of the nanostructure coverage on the surface pattern is also designed in view of these structures.

In addition, soft and stable PDMS materials with Young's moduli as low as ~250 KPa can be prepared, which are compatible with the fragile nature of CTCs. In addition, the desired surface patterns can be replicated to lower modulus materials, such as poly(ethylene glycol methacrylate) (PEGMA) and polyacrylamide (PA).

Figure 3:
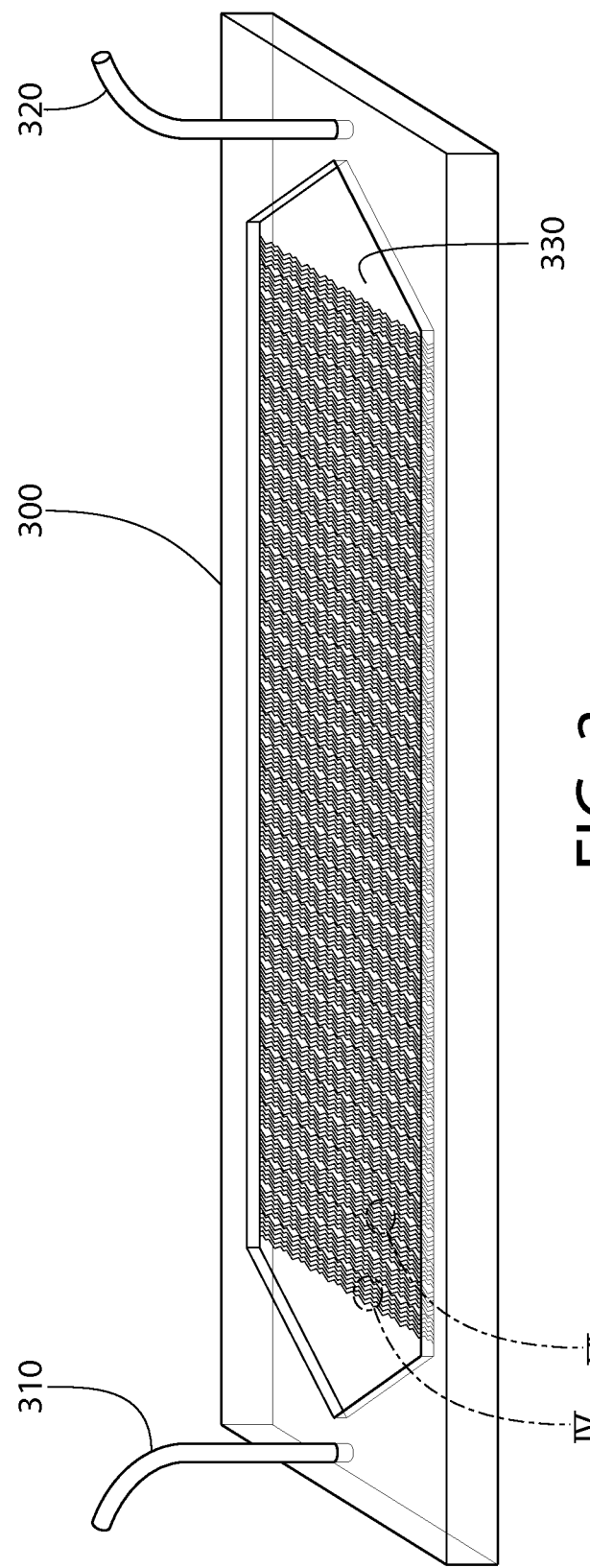
FIG. 3 depicts a schematic of an exemplary microfluidic device of the present invention.

A typical integrated microfluidic testing device is illustrated in FIG. 3. The fabricated hierarchical surface may be covered with a PDMS transparent top with two parallel channels or a single channel encapsulating a half flat and half rippled surface via PDMS-PDMS or $O_2$ plasma bonding. Some embodiments provide a transparent device that allows in-situ observation of the cell capture by fluorescence microscopy.

In some embodiments, the channel height may vary from about 20 μm to about 60 μm. In some embodiments, cells or microparticles will be driven through the microchannels by a programmable syringe pump. The images can be captured by a cooled CCD camera.

Flat covers, rippled complimentary covers, and rippled non-complimentary covers may all be viable options. To create two self-aligned PDMS ripple surfaces, PDMS can be cast on a PDMS rippled surface. After curing, the rippled interface can be separated by inserting a thin glass cover slip or wire between the two rippled surface and monitored under an inverted optical microscope. In such an embodiment, the two PDMS strips will be self-aligned, each having complementary ripples on their surface.

In some embodiments, the devices of the present invention provide multiscale cell adhesion dynamics that model cell transport in flow and interaction between the wrinkled surfaces while keeping ligand-receptor binding details. Some embodiments provide a hierarchical wrinkle surface having dual size matching: microscale sinusoidal ripples with tunable wavelength to match the cell size, and nanopillars with tunable size/density to be complimentary with that of microvilli on the cell surface. Without being bound by theory, it is believed that the unique dual-size matching significantly and selectively enhances the capture and adhesion of cells of a particular size and surface property, and avoids non-specific trapping or possible cell damage.

In some embodiments, the present invention provides a patterned distribution of captured cells throughout separated troughs, which allows fast/automatic cell counting. An additional advantage provided by the devices of the present invention is that the hierarchical structure can be mass produced, making it attractive for potential integration in global health care devices.

In some embodiments, the devices of the present invention comprise a wavy micropatterned microfluidic device for capturing circulating tumor cells from whole blood with high efficiency, selectivity and throughput.

In some embodiments, a capturing agent is immobilized on the substrate. In some embodiments, a capturing agent is immobilized on the substrate which selectively captures circulating tumor cells while not interacting with other cells present in the whole blood.

In some embodiments, the substrate surface has repetitive wave-herringbone structures. In some embodiments, the substrate surface has repetitive wave-herringbone structures, which can induce a rotational flow. In some embodiments, the rotational flow can enhance the collision of circulating tumor cells with the substrate surface, therefore increasing the capture efficiency of the circulating tumor cells.

In some embodiments, the wave-herringbone surface pattern (topography of the substrate surface) differs from a traditional herringbone groove structure in the fact that it is comprised of sinusoidal waves extending in two directions as opposed to sharp ridges. This structure can also keep the morphology of circulating tumor cells intact, which is important for various post-analyses.

In some embodiments, the proposed microfluidic device is comprised of a substrate surface and a cover, which are combined to form a flow channel. Some embodiments provide an inlet reservoir and an outlet reservoir. In some embodiments, the inlet reservoir and/or the outlet reservoir are punched in the device.

In some embodiments, a sample is injected through the inlet reservoir, passing through the flow channel and then reaching the outlet reservoir. In some embodiments, the sample is a biological sample. In some embodiments, the biological sample is whole blood.

In some embodiments, the rotational flow induced by the repetitive wave-herringbone structures can enhance the capture efficiency of circulating tumor cells while all other cells flow through in a streamlined fashion reaching the outlet reservoir.

In some embodiments, the applied shear rate to the device can range from 10 s$^{-1}$ to 2000 s$^{-1}$. In some embodiments, the applied shear rate to the device can range from 30 s$^{-1}$ to 500 s$^{-1}$.

In some embodiments, the wave-herringbone surface pattern has a characteristic angle ranging from about 30 degrees to about 120 degrees. In some embodiments, the lateral length of this structure can range from about 100 μm to about 1000 μm, and the longitudinal length is calculated according to the characteristic angle.

In some embodiments, the wave-herringbone surface pattern can have values ranging from 40 μm to 100 μm in terms of wavelength and 13 μm to 33 μm in terms of amplitude. In some embodiments, the depth of the flow channel is from about 40 μm to about 100 μm, and the overall size of the flow channel is from about 200 μm to about 4000 μm in terms of width and about 0.5 cm to about 1.5 cm in terms of length.

Some embodiments of the present invention provide a capture efficiency of greater than 80%, with high purity. Some embodiments of the present invention provide a capture efficiency of greater than 85%, with high purity. While other embodiments provide a capture efficiency of up to 90%, with high purity. Some embodiments of the present invention provide a capture efficiency of greater than 95%, with high purity. Some embodiments of the present invention provide a capture efficiency of greater than 96%, with high purity. Some embodiments of the present invention provide a capture efficiency of greater than 97%, with high purity. Some embodiments of the present invention provide a capture efficiency of greater than 98%, with high purity. Some embodiments of the present invention provide a capture efficiency of greater than 99%, with high purity.

As shown in FIG. 3, some embodiments of the present invention provide a device comprising an inlet and an outlet. In some embodiments, two pieces of tubing serve as the inlet and the outlet. In some embodiments, the sample is injected through the inlet and passes to the outlet. In some embodiments, the bottom layer of the channel is comprised of a plurality of smooth curves, with the left section depicting these smooth curves; and the blue spheres represent circulating tumor cells.

In some embodiments, the device achieves higher capture efficiency when compared with other methods, due to the enhanced rotational flow induced by the wave-herringbone surface pattern.

In other embodiments, the device allows for easy fabrication without the need for a cleanroom, which is in contrast to traditional fabrication processes which need soft-photolithography to make the mold in the cleanroom.

In some embodiments, the devices can achieve a higher throughput, due to the large cross-area in the device. This advantage can reduce the time for the blood test, thus significantly increasing the efficiency.

In some embodiments, the device has the ability to capture circulating tumor cells while maintaining the cells' natural morphology, due to the smooth sinusoidal curve patterning.

In some embodiments, the device comprises smooth sinusoidal wave patterns which force cells to roll over the curve and reach the trough. Thus, cell imaging after the flow test simply requires clinicians/researchers to scan the trough regions to gain the information of the captured circulating tumor cells.

In some embodiments, the device is used for the high efficiency capture of other biological cells or analytes after the immobilization of corresponding capturing agents.

In some embodiments, the lateral dimension of the wave-herringbone structure can be decreased to the order of 1 μm and increased to the order of 1 mm. In some embodiments, the wavelength can be decreased to the order of 10 μm and increased to the order of 200 μm. In some embodiments, the amplitude can then be accordingly decreased to the order of 3 μm and increased to the order of 60 μm. In some embodiments, the depth of channel can be decreased to the order of 20 μm and increased to the order of 200 μm. In still further embodiments, the overall size of the flow channel can also be decreased to the order of 10 μm and increased to the order of 1 mm.

In some embodiments, the devices comprise micro-scale sinusoidal ripples and herringbone structures. In some embodiments, the devices comprise micro-scale sinusoidal ripples and herringbone structures that generate micro-vortices to enhance cell-wall collision, provide larger adhesion area, avoid non-specific cell adhesion and possible cell damage, and/or enable accurate cell counting. In some embodiments, these nanostructures will complement microvilli on cell membranes; and thus, improve both interaction specificity and cell capturing efficiency.

In some embodiments, cell imaging techniques are incorporated in the proposed device to detect the signals of cell capture.

In some embodiments, devices of the present invention are used by physicians or clinicians to capture circulating tumor cells in a patient's whole blood, which then allows for various post-analyses to be carried out on intact cells. For example, with certain techniques, devices of the present invention could indicate the number of captured circulating tumor cells, which could serve as an indicator for specific diseases. In other embodiments, after circulating tumor cells are captured, the cells could be analyzed to reveal their genetic and protein information, thus providing a guide for potential treatments, and even the possibility of personalized treatment.

In some embodiments, the wave-herringbone surface pattern forms the surface of the microfluidic channel. In some embodiments, the channel itself is a hollow channel while the pattern shows on the surface.

Figure 1:
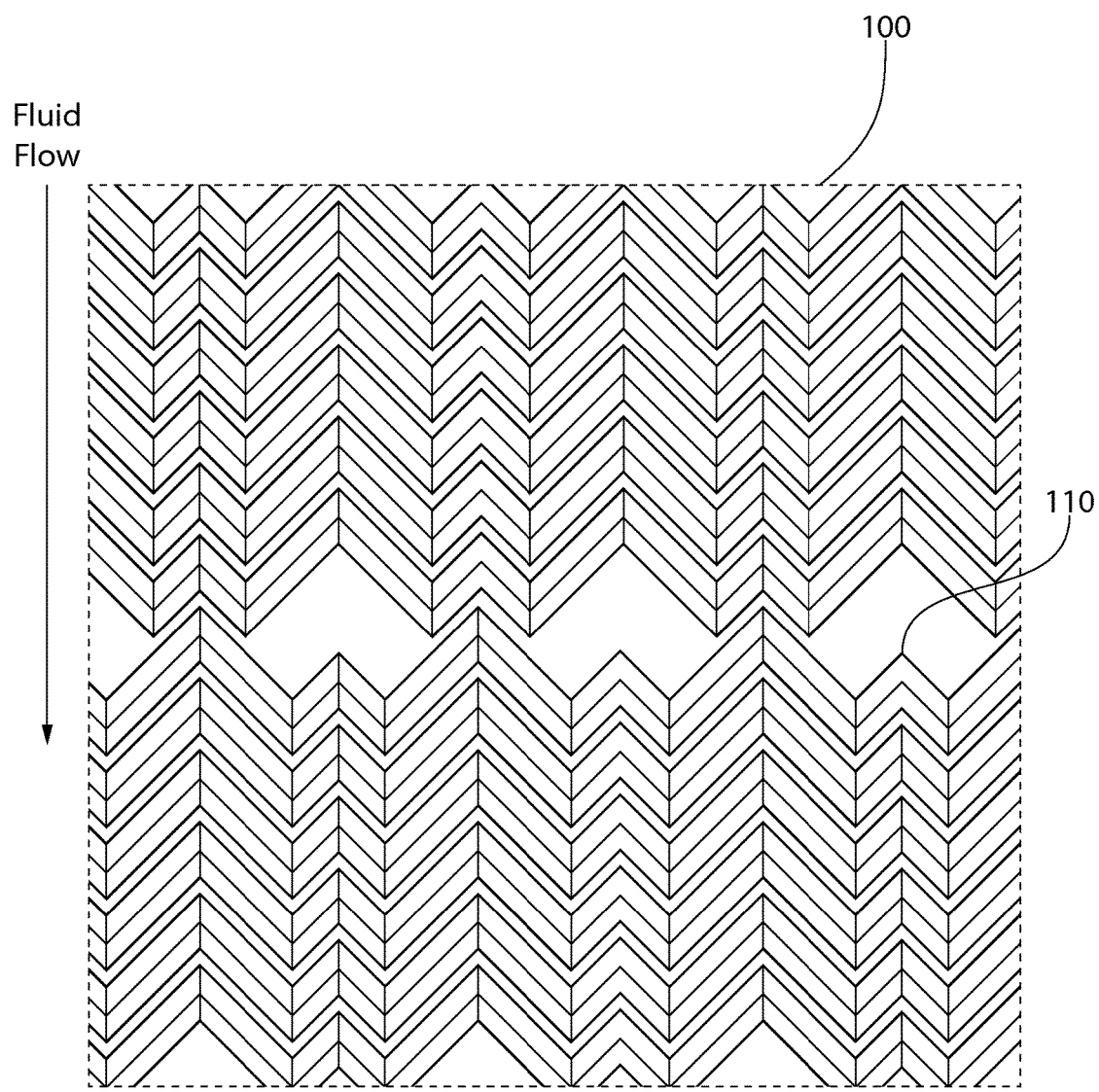
FIG. 1 depicts a prior art surface pattern.

Referring now to the Figures, FIG. 1 depicts a surface pattern employed by conventional devices used to separate particles from a fluid. As shown in FIG. 1, the surface patterns used to separate particles in conventional devices have an apex 110 with a sharp corner, which reduces capture efficiency and can damage cells.

Figure 2:
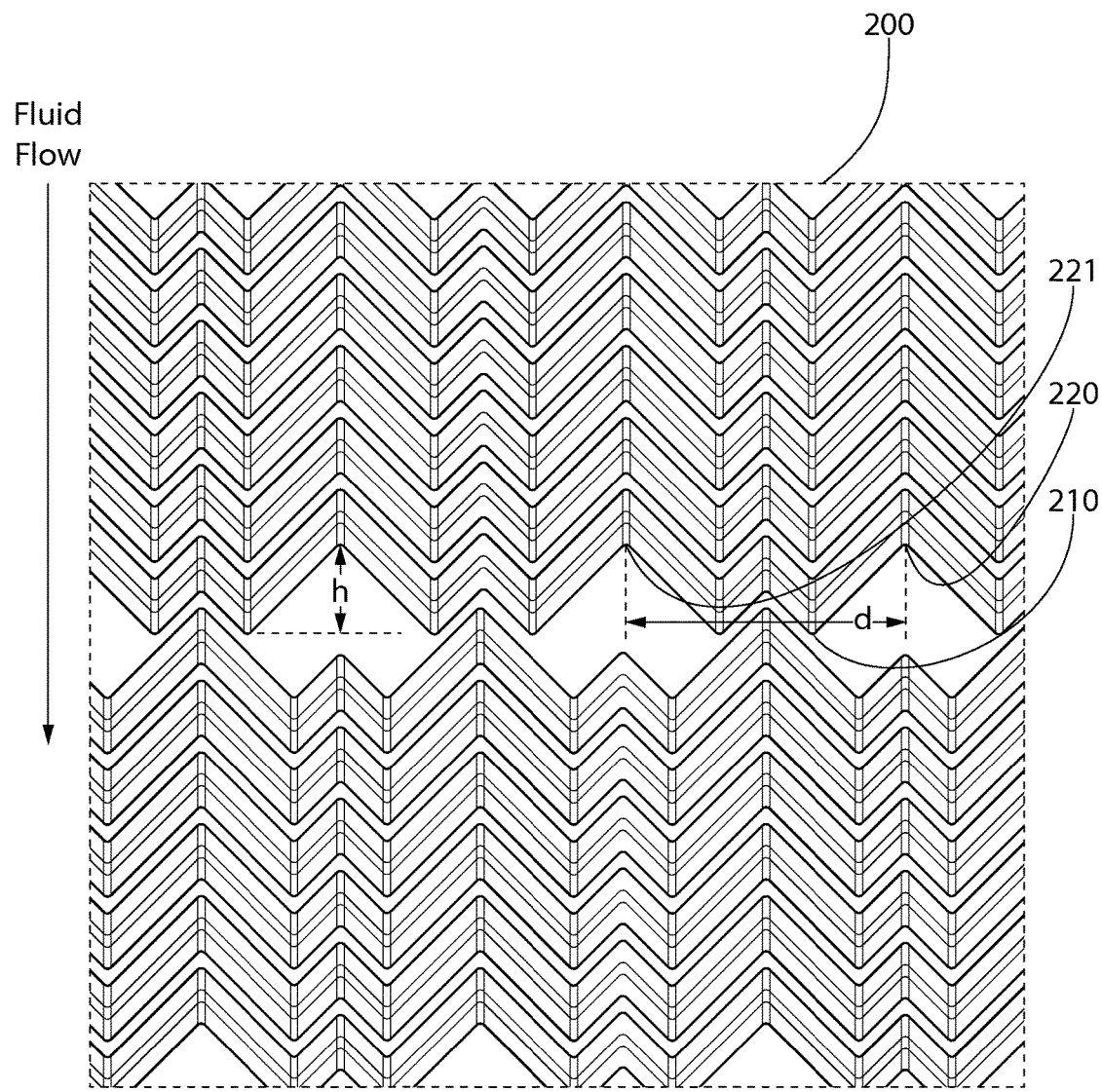
FIG. 2 depicts an exemplary capture bed of the present invention having a wave-herringbone surface pattern.

In contrast, the surface patterns of the present invention, for example as depicted in FIG. 2, provide a smoother apex 220, which increases the capture efficiency and avoids damage to the cells. FIG. 2 also depicts height (h) spanning between apex 220 and the base of the surface pattern 210. Height (h) is an important feature as the amplitude vs. wavelength ratio of the surface pattern has been designed for optimal capture efficiency. In some embodiments, the ratio of amplitude to wavelength is from about 1:2 to about 1:4. In some embodiments, the ratio of amplitude to wavelength is about 1:3. In some embodiments, the distance (d) from apex 220 to apex 220 is from about 30 microns to about 60 microns. In some embodiments, distance (d) is from about 35 microns to about 55 microns. In some embodiments, distance (d) is from about 40 microns to about 50 microns. In some embodiments, distance (d) is about 45 microns. In some embodiments, distance (d) is about 50 microns.

FIG. 3 provides a plan view of an exemplary microfluidic device 300 of the present invention. As shown, in FIG. 3, some embodiments of the present invention include an inlet 310 and an outlet 320. The diameters of the inlet 310 and outlet 320 apertures can vary. A fluid flow across the capture bed 330 of from about 358 ul/hr to about 5800 ul/hr is typically applied In addition, FIG. 3 depicts the location of the hierarchical surface pattern in the capture bed 330 of an exemplary microfluidic device 300.

The side view zoom depicted in FIG. 4, is an exploded view of the section identified as "IV" in FIG. 3. As FIG. 4 demonstrates, surface patterns of the present invention have a much smoother surface than conventional particle separation devices.

Figure 5:
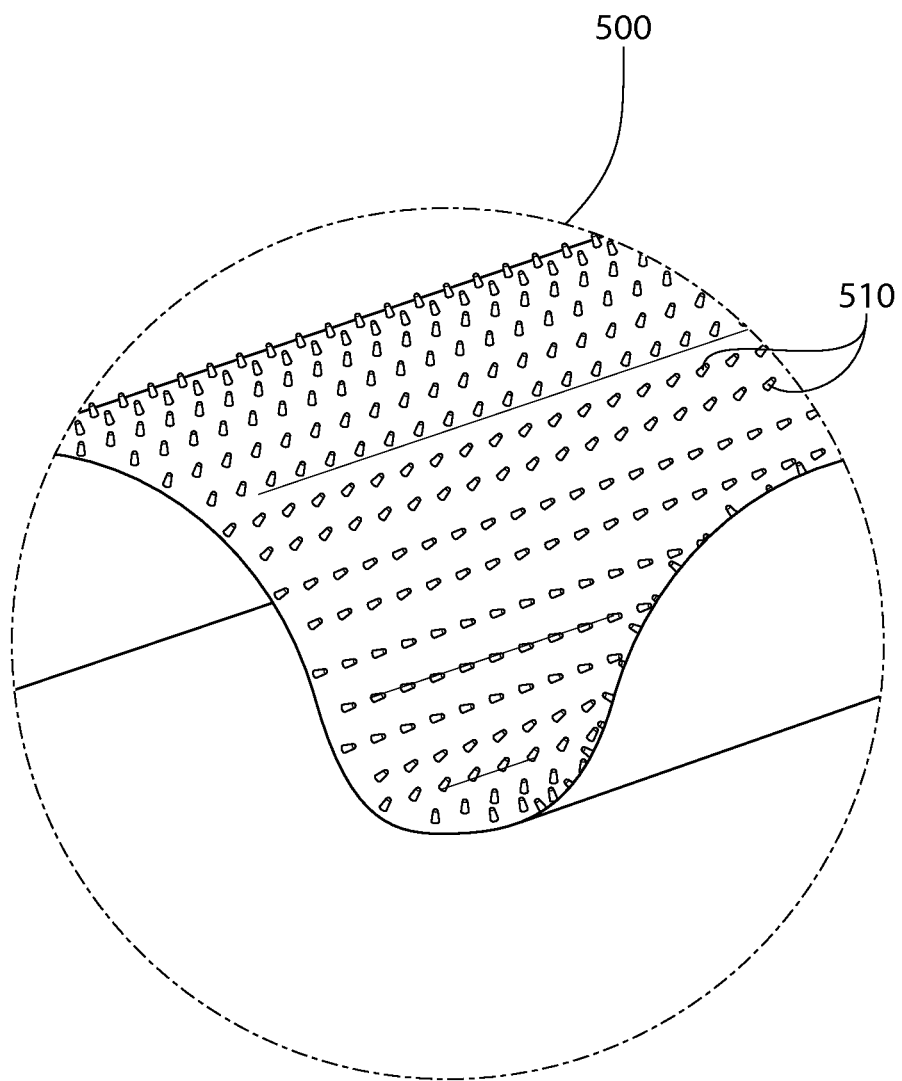
FIG. 5 depicts an exemplary hierarchical surface pattern of the present invention having nanopillars.

FIG. 5 provides an exploded view of the section identified as "V" in FIG. 4. As shown in FIG. 5, the hierarchical surface patterns of the present invention include nanostructures 510. FIG. 5 specifically depicts these nanostructures in the form of nanopillars. However, nanostructures 510 can also take the form of nanospheres or protrusions of almost any shape and dimension, as long as it provides the requisite complementarity to the surface structure of the cell being captured from the sample, e.g. the microvilli of a circulating tumor cell.

In some embodiments, the nanostructures have a height of about 1 micron, a diameter of about 100 nm. In some embodiments, the nanostructures are spaced at about 200 nm apart on the surface pattern. In some embodiments, the nanostructure diameter ranges from about 120 nm to about 1100 nm. In some embodiments, the nanostructures are spaced at a distance of from about 50 nm to about 800 nm from each other. Nanostructure spacing has been found to directly impact the capture efficiency and specificity.

FIG. 6 depicts an exploded view of the section identified as "VI" in FIG. 3. Specifically, FIG. 6 depicts the capture of circulating tumor cells 610, using an exemplary hierarchical surface pattern of the present invention 600. As shown in FIG. 6, the circulating tumor cells 610 have microvilli 611. These microvilli 611 protrude from the surface of the circulating tumor cell 610. FIG. 6 also depicts red blood cells 620 (RBC) which are selectively separated from the circulating tumor cells 610 by the hierarchical surface pattern of the present invention 600.

The invention will be described in greater detail by way of specific examples. The following examples are offered for illustrative purposes and are not intended to limit the invention in any manner. Those skilled in the art will readily recognize a variety of noncritical parameters, which can be changed or modified to yield essentially the same results.

EXAMPLES

Example 1

Preliminary studies have been carried out by injecting 2 μm fluorescent particles into a PDMS microchannel consisting of half rippled (20 μm wavelength) and half flat surface under flow shear rates of $30^{-1}$ and $90\ s^{-1}$ to study the particle distribution. The individual particles and their movement are monitored in situ. Very few binding events occurred on the flat surface. In contrast, many microparticles were clearly bound on the rippled surface, most of which were located on the same plane as the troughs of the ripples, which is favorable for cell counting.

Example 2

Four cells are released at the inlet of a 40 μm high channel under a shear rate of 20 s-1 and periodic boundary conditions are applied at the inlet and outlet. After three seconds, two cells are captured on the rippled surface while no cells are captured on the flat surface. The number of cells captured on a rippled surface is found to be much larger than that on a flat surface, which demonstrates that the rippled surface helps cell margination and contact with the wall surface. The cell-wall interaction is accurately modeled with ligand-receptor binding/breaking details. Besides increased capture rate, the adhesion strength of the rippled surface is also predicted to be much higher than that of the flat surface.

Example 3

An exemplary device of the present invention is tested with lung cancer epithelial cell NCI-H1650 and the prostate cancer cell PC3, which have been widely used as model cell lines for optimizing CTC diagnostics. The interior surfaces of the test device is functionalized though silane chemistry and biotinylated antibody, followed by blocking with albumin. For substrates other than PMMA, specific antibodies are coated onto them through standard chemistry to functionalize the hydroxyl group, carboxyl group (directly or from hydrolyzed ester group), amine group, or simply physisorption. Cell suspensions containing 10-10000 cells/mL in buffer or spiked in healthy donor's blood are flowed through the microchips at the optimal flow shear rate range as determined by computational and microparticle capture studies. The cell concentration range is designed to cover the CTC concentration in cancer patients of different stages. The captured cells are stained by anti-CD45 (a leukocyte marker), anti-cytokeratin (a specific marker for tumor cells originated from epithelial), and DAPI (nucleus stain). The number of captured H1650/PC3 cells and leukocytes are counted under an optical microscope to determine the capture efficiency and purity. The location of captured cells on the hierarchical surfaces is also documented. The capture yields on flat, micro-feature only, nano-feature only and hierarchical surfaces are compared.

TABLE 1

| Surface Pattern | Capture Efficiency (%) |
| --- | --- |
| Flat | 6.2 |
| Wave | 26.8 |
| Herringbone | 76.5 |
| SP 1 | 86.7 |

The results described in Table 1 (above) demonstrate that an exemplary device of the present invention, having a rippled herringbone (or wave-herringbone) surface pattern (SP 1), has the highest capture efficiency—around 90%. These results demonstrate the unexpected improvement in capture efficiency provided by an exemplary surface pattern of the present invention.

It is intended that any patents, patent applications or printed publications, including books, mentioned in this patent document be hereby incorporated by reference in their entirety.

As those skilled in the art will appreciate, numerous changes and modifications may be made to the embodiments described herein, without departing from the spirit of the invention. It is intended that all such variations fall within the scope of the invention.

The invention claimed is:

1. A device for capturing a biological cell from a sample, the device comprising:
 a capture bed comprising:
  a wave-herringbone surface pattern having a ratio of amplitude-to-wavelength that is 1:2; and
  a plurality of nanostructures;
 wherein the wave-herringbone pattern and the plurality of nanostructures are integrated on a single surface; and
 wherein the nanostructures are equidistantly spaced in the capture bed.

2. The device according to claim 1, wherein the nanostructures are selected from the group consisting of nanopillars; nanospheres; and a combination thereof.

3. The device according to claim 1, wherein the nanostructures each have an average diameter of from 100 nm to 1500 nm.

4. The device according to claim 1, wherein the equidistant spacing between nanostructures be selected from a distance ranging from 100 nm to 250 nm.

5. The device according to claim 1, wherein the wave-herringbone surface pattern comprises sinusoidal-like waves extending in two directions.

6. The device according to claim 1, wherein the wave-herringbone surface pattern is configured to form channels in the capture bed.

7. The device according to claim 6, wherein the channels have a height of from 20 μm to 100 μm.

8. The device according to claim 1, further comprising:
 an inlet; and
 an outlet;
 wherein the outlet is positioned at a distance from the inlet; and wherein the sample flows from the inlet to the outlet.

9. The device according to claim 8, wherein the sample flows from the inlet to the outlet at a rate sufficient to capture a biological cell from the sample.

10. The device according to claim 1, wherein the capture bed further comprises a capturing agent.

11. The device according to claim 10, wherein the capturing agent is selected from the group consisting of: an antibody; and an aptamer.

12. A kit for isolating a target cell from a sample comprising the device according to claim 1; and instructions for using said device.

* * * * *

UNITED STATES PATENT AND TRADEMARK OFFICE
CERTIFICATE OF CORRECTION

| | |
|---|---|
| PATENT NO. | : 10,401,362 B2 |
| APPLICATION NO. | : 14/618246 |
| DATED | : September 3, 2019 |
| INVENTOR(S) | : Yaling Liu |

It is certified that error appears in the above-identified patent and that said Letters Patent is hereby corrected as shown below:

In the Specification

Column 1 Line 12 prior to the section entitled "Background," please insert the following header and paragraph:
--Statement Regarding Government Interests
This invention was made with government support under 1264808 awarded by the National Science Foundation. The government has certain rights in the invention.--

Signed and Sealed this
Thirty-first Day of May, 2022

Katherine Kelly Vidal
Director of the United States Patent and Trademark Office